United States Patent [19]

Tolman et al.

[11] Patent Number: 4,863,927
[45] Date of Patent: Sep. 5, 1989

[54] 1-(2-HYDROXYMETHYL)CYCLOALKYLMETHYL)-5-SUBSTITUTED URACILS

[75] Inventors: Richard L. Tolman, Warren; Wallace T. Ashton, Clark, both of N.J.

[73] Assignee: Merck & Co., Inc., Rahway, N.J.

[21] Appl. No.: 48,290

[22] Filed: May 11, 1987

[51] Int. Cl.$^4$ .................. A61K 31/505; C07D 239/54; C07D 239/55

[52] U.S. Cl. .................. 514/274; 544/309; 544/313; 544/314

[58] Field of Search ............ 544/313, 314, 309; 514/274

[56] References Cited

U.S. PATENT DOCUMENTS

| | | | |
|---|---|---|---|
| 4,027,025 | 5/1977 | Schaeffer | 544/254 |
| 4,146,715 | 3/1979 | Schaeffer | 544/277 |
| 4,199,574 | 4/1980 | Schaeffer | 544/276 |
| 4,347,360 | 9/1982 | Ogilvie | 544/276 |
| 4,355,032 | 10/1982 | Verheyden et al. | 544/276 |
| 4,424,211 | 1/1984 | Jones et al. | 544/309 |
| 4,617,304 | 10/1986 | Ashton et al. | 514/261 |

FOREIGN PATENT DOCUMENTS

| | | |
|---|---|---|
| 201289 | 11/1986 | European Pat. Off. |
| 3608606 | 9/1986 | Fed. Rep. of Germany |
| 1284 | 3/1987 | World Int. Prop. O. |

OTHER PUBLICATIONS

Colla et al, J. Med. Chem. 1983, 26, 602–604, "Synthesis and Antiviral Activity of Water-Soluble Esters of Acyclovir".

Baerwolff et al, CA 100-156945f (1984) "5-(2,2-Disubstituted) Uracil Derivatives".

Cooper, CA 100-91365v "Penetrating Topical Pharmaceutical Compositions Containing 9-(2-Hydroxyethoxymethyl)Guanine".

Verheyden et al, CA 100-7067u "Substituted 9-(1 or 3-Monoacyloxy or 1,3-Diacyloxy-2-Propoxymethyl) Purines as Antiviral Agents".

Griengl et al, CA 100-210358g "Deoxyuridine Derivatives and Their Use as Pharmaceuticals".

Johansson et al, CA 104-50735e "Guanine Derivatives, Their Pharmaceutical Composition and Selectivity Combatting Viruses".

R. J. Klein, Antiviral Res., Suppl. 1, pp. 111–120, (1985).

*Primary Examiner*—Cecilia Shen
*Attorney, Agent, or Firm*—Richard S. Parr; Hesna J. Pfeiffer

[57] ABSTRACT

1-[2-(Hydroxymethyl)cycloalkylmethyl]-5-substituted uracils which are herpes simplex viral thymidine kinase inhibitors, their acyl derivatives, and their pharmaceutically-acceptable salts; pharmaceutical formulations containing these compounds; the treatment of DNA viral, particularly herpes viral, infections with these compounds; methods of preparing these compounds; and novel intermediates useful in their preparation.

6 Claims, No Drawings

1-(2-HYDROXYMETHYL)CYCLOALKYLMETHYL)-5-SUBSTITUTED URACILS

BACKGROUND OF THE INVENTION

The use of purine and pyrimidine derivatives as antiviral compounds is known. For example, U.S. Pat. No. 4,27,025 discloses 8-azapurine derivatives, such as 9-(2-hydroxyethoxymethyl)-8-azaguanine and 9-(2-benzoyloxyethoxymethyl)-8-azaguanine, as anti-viral compounds. U.S. Pat. No. 4,146,715 discloses 2-amido-9-(2-acyloxyethoxymethyl)hypoxanthines and U.S. Pat. No. 4,199,574 discloses that 9-(2-hydroxyethoxymethyl) and related derivatives of certain 6-, and 2,6-substituted purines have anti-viral activity. U.S. Pat. Nos. 4,347,360 and 4,355,032 disclose that 9-[[2-hydroxy-1-(hydroxymethyl)ethoxy]methyl]guanine (gancyclovir) has antiviral activity and Colla et al., *J. Med. Chem.*, 26, 602–604 (1983) and published European Patent Application No. 95 813 disclose esters and ethers of acyclovir. European Patent Application Publication No. 85 424 discloses acyl derivatives of 9-(1,3-dihydroxy-2-propoxymethyl)guanine, and U.S. Pat. No. 4,617,304 discloses thymidine kinase substrates having a 3-membered cycloalkyl group in the side chain of a purin-9-yl or pyrimidin-1-yl derivative.

U.S. Pat. No. 4,424,211 discloses antiviral activity for (E)-5-(2-bromovinyl)-2-deoxyuridine (BVDU) and related compounds, with esters of BVDU having antiviral activity being disclosed in published EPO application No. 97 039. PCT International Application No. WO 84 00,759 discloses antiviral activity for 5-(2-chloroethyl)-2'-deoxyuridine (CEDU) and related compounds.

Inhibition of herpes simplex type I (HSV-1) thymidine kinase by certain 9-(hydroxyalkyl)- and 9-(hydroxyalkenyl)guanines has been disclosed in published EPO Application 146 516, but the antiviral activity of the compounds disclosed has been attributed to selective phosphorylation by the HSV thymidine kinase and subsequent inhibition of the viral DNA polymerase (A Larsson et al., *Antimicrob. Agents-Chemother.*, 30, 598–605 (1986).

Herpes simplex virus infections are currently best treated with acyclovir (ACV), which is a selective substrate for HSV thymidine kinase and (as the triphosphate) inhibits HSV DNA polymerase. ACV has been shown to be effective in treating primary herpes infections, but does not prevent establishment of latent infection.

Known antiviral agents, such as acyclovir, gancyclovir and BVDU, however, are susceptible to enzymatic phosphorylation in non-infected cells to a small extent and thus have an effect upon nucleotide pool sizes and, by means of DNA polymerase, can be incorporated into DNA, thus increasing mutagenicity hazards.

It was therefore an object of the present invention to identify novel, viral thymidine kinase (TK) inhibitory compounds which are not TK-substrates, but which might be effective in the prevention of viral reactivation or in the abolition of latency. Another object was to identify compounds which have utility and safety in the treatment of specific members of the herpes group (i.e., herpes simplex, types 1 and 2, and varicella zoster), which express their own thymidine kinases. A further object of the present invention was to identify pharmaceutical formulations for the effective administration of the novel compounds of the invention. Still another object is to provide methods for the preparation of the novel compounds of the present invention.

DESCRIPTION OF THE INVENTION

The present invention relates to herpes simplex viral thymidine kinase inhibitors and, more particularly, to 1-[2-(hydroxymethyl)cycloalkylmethyl]-5-substituted-uracils of Formula I:

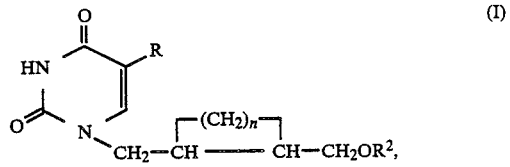

wherein R is H, halogen, $C_1$–$C_4$-straight or branched-chain alkyl, 2-halovinyl, or 2-haloethyl; $R^2$ is H or

wherein $R^1$ is a straight- or branched-chain alkyl group of 1 to 12 carbon atoms or phenyl or naphthyl; and n is 2 to 6;
and to pharmaceutically-acceptable salts thereof.

Both the E and Z isomers, each of which is a pair of enantiomers, of which one enantiomer may be a better inhibitor than its antipode, are included in these definitions.

Preferred compounds according to the present invention include:
1-[(Z)-2-(hydroxymethyl)cyclobutylmethyl]thymine;
1-[(Z)-2-(hydroxymethyl)cyclopentylmethyl]thymine;
1-[(Z)-2-(hydroxymethyl)cyclohexylmethyl]thymine;
1-[(E)-2-(hydroxymethyl)cyclohexylmethyl]thymine;
1-[(Z)-2-(hydroxymethyl)cycloheptylmethyl]thymine;
1-[(Z)-2-(hydroxymethyl)cyclooctylmethyl]thymine;
5-bromo-1-[(Z)-2-(hydroxymethyl)cyclohexylmethyl]uracil;
5-ethyl-1-[(Z)-2-(hydroxymethyl)cyclohexylmethyl]uracil;
5-[(E)-2-bromovinyl]-1-[(Z)-2-(hydroxymethyl)cyclohexylmethyl]uracil; and
5-(2-chloroethyl)-1-[(Z)-2-(hydroxymethyl)cyclohexylmethyl]uracil.

Particularly preferred compounds according to the present application then include:
1-[(Z)-2-(hydroxymethyl)cyclohexylmethyl]thymine; and
5-[(E)-2-bromovinyl]-1-[(Z)-2-(hydroxymethyl)cyclohexylmethyl]uracil.

The compounds disclosed herein have biological or chemical properties which give them advantages in the treatment of the various diseases and ailments associated with members of the herpes group of viruses which express their own thymidine kinases, and which compounds are safe to use, and particularly possess utility in the treatment of latent infections. Furthermore, the corresponding acyl derivatives of the compounds of Formula I are preferred because they have formulation and pharmacodynamic advantages, that is, the acyl group can impart aqueous or oil solubility which is an asset in oral or topical formulation and can facilitate intestinal uptake or passage through the stratum corneum and can also act to extend plasma half-life.

The compounds of Formula I may be prepared by alkylation of a 5-substituted uracil with a protected 2-(hydroxymethyl)cycloalkylmethyl halide or arene- or alkanesulfonate followed by deprotection using standard methods. One of the two hydroxyl groups of a cycloalkane-1,2-dimethanol is protected, e.g. by acylation with an equivalent of benzoyl chloride in the presence of a base such as pyridine. The remaining hydroxyl group is converted to a leaving group by standard methods. For example, it may be transformed to a bromo group with carbon tetrabromide and triphenylphosphine, to an iodo group with methyltriphenoxyphosphonium iodide, or to a p-toluenesulfonate group with p-toluenesulfonyl chloride in the presence of a base such as pyridine. The alkylation is preferably carried out at 50° C. to 100° C. in any of a variety of suitable solvents, but especially a polar, aprotic solvent such as N,N-dimethylformamide or dimethyl sulfoxide, with a base such as anhydrous potassium carbonate to generate the uracil anion. Where the leaving group is less reactive than iodo, the reaction may be assisted by the addition of sodium iodide. By-products due to alkylation at $N^3$ or dialkylation at $N^1$ and $N^3$ may be removed chromatographically if necessary. Where the protecting group of the alkylated product is acyl, it may be removed by standard methods such as aqueous methylamine, methanolic ammonia, or methanolic sodium methoxide.

Alternatively, compounds of Formula I may be prepared by the Hilbert-Johnson method and its variants. Thus, a 5-substituted-2,4-dialkoxy (or disilyloxy) pyrimidine is reacted at elevated temperature with a protected 2-(hydroxymethyl)cycloalkylmethyl bromide or iodide. The resulting 1-alkylated-4-alkoxy (or silyloxy) pyrimidin-2(1H)-one is hydrolyzed to give a 1-alkylated-5-substituted-uracil. The side chain protecting group may then be removed in the same step or in a separate step.

The acyl derivatives are preferably prepared by reacting the compounds of Formula I with the appropriate acyl halide, acid anhydride, or other activated acyl species in the presence of an appropriate cosolvent such as, for example, pyridine-dimethylformamide. In reactions with acyl halide or acid anhydrides the reaction rate and yield can be increased by the addition of a tertiary amine such as triethylamine, with 4-dimethylaminopyridine being an effective catalyst. Other activated acyl species may be prepared by reaction of the acid with a suitable activating agent such as, for example, 1,1'-carbonyl-diimidazole, N,N'-dicyclohexylcarbodiimide or by acylation of N-hydroxysuccinimide or 1-hydroxybenzotriazole by known methods.

Compounds of the present invention are potent and selective inhibitors of herpes simplex viral thymidine kinase. As such, their toxicity to mammalian cells is minimal. These compounds additionally are resistant to enzymatic phosphorylation, even in virus-infected cells, and therefore, mutagenicity hazards are minimized, in that inhibition of DNA polymerase and incorporation into DNA are avoided. These compounds in effect mimic the thymidine kinase deficiency of TK$^-$ mutants. HSV TK$^-$ mutants tend to be less pathogenic, have diminished ability to establish latent infections, and may be incapable of reactivation if latent infection occurs [R.J. Klein, *Antiviral Res.*, Suppl. 1, 111 (1985) and references therein]. The invention is intended for the treatment or prophylaxis of herpes (especially herpes simplex) virus infections in man and may be of particular utility in preventing recurrence of latent virus infection.

The compounds of the present invention may be administered to mammalian or avian species either individually or in combinations in dosage levels effective to impart a viral thymidine kinase-inhibiting activity. Typically such therapeutically-effective levels are from about 0.01 to about 200 mg/kg/day. The compounds of the present invention may be formulated according to accepted pharmaceutical practice for administration orally, topically or by injection according to known methods. Suitable oral dosage forms include tablets, capsules, elixirs or powders, while solutions or suspensions in, for example, phosphate buffered saline or water are suitable for injection. Examples of suitable topical formulations are gels, ointments, solutions or suspensions.

The following Examples illustrate the present invention without, however, limiting the same thereto. All temperatures are expressed in degrees Celsius.

EXAMPLE 1

Synthesis of 1-[(Z)-2-(hydroxymethyl)cyclohexylmethyl]thymine

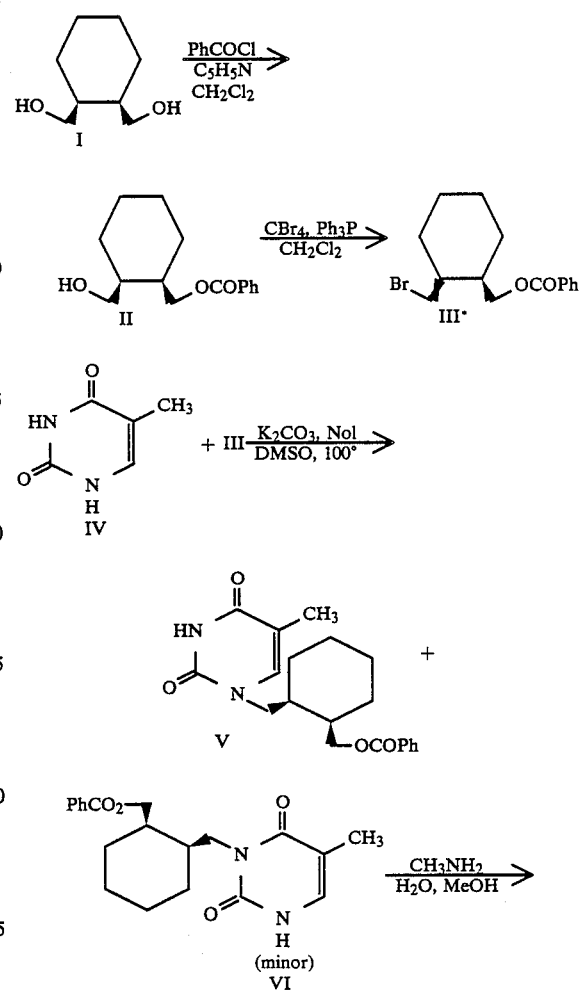

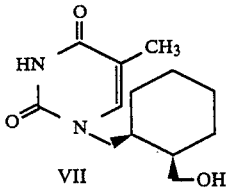

A. (Z)-2-(Benzoyloxymethyl)cyclohexanemethanol (II)

To a solution of 50.0 g (0.346 mole) of cis-1,2-cyclohexanedimethanol (I) and 35 ml of pyridine in 400 ml of methylene chloride stirred under nitrogen at 0° C. was added dropwise 40.25 ml (48.7 g, 0.346 mole) of benzoyl chloride. After completion of the addition, the mixture was allowed to warm to room temperature and was stirred overnight. The mixture was concentrated in vacuo, and the residue was partitioned between ethyl acetate and water. The organic layer was washed with water, then dried (MgSO4), filtered and concentrated. The residual oil was chromatographed on a column of silica gel (elution with 9:1 hexane-ethyl acetate followed by 4:1 hexane-ethyl acetate) to give 43.8 g (81%) of the product as an oil, which was homogeneous by TLC (9:1 hexane-ethyl acetate). The structure was confirmed by NMR (CDCl3).

B. (Z)-2-(Benzoyloxymethyl)cyclohexylmethyl bromide (III)

A solution of 43.0g (0.173 mole) of (Z)-2-(benzoyloxymethyl)cyclohexanemethanol (II) and 86.2 g (0.26 mole) of carbon tetrabromide in 400 ml of dry methylene chloride was stirred at room temperature as a solution of 54.3 g (0.207 mole) of triphenylphosphine in 100 ml of methylene chloride was added dropwise over a period of 2 hours. After 4 days of stirring room temperature, TLC (4:1 hexane-ethyl acetate) indicated complete conversion of II to product (greater $R_f$). Concentration of the mixture gave a dark residue, which was triturated with 1:1 hexane-ethyl acetate. The insoluble solid was removed by filtration. The residue from concentration of the filtrate was chromatographed on a column of silica gel (elution with 99:1 and then 97:3 hexane-ethyl acetate), yielding 43.8g (81%) of the product as an oil, which was homogeneous by TLC (9:1 hexane-ethyl acetate). The structure was confirmed by NMR and mass spectrum.

Elemental analysis. Calcd. for $C_{15}H_{19}BrO_2$: C, 57.89%; H, 6.15%; Br, 25.67%. Found: C, 58.03%; H, 6.16%; Br, 25.76%.

C. 1-[(Z)-2-(Benzoyloxymethyl)cyclohexylmethyl]thymine (V)

A mixture of 630 mg (5 mmole) of thymine (IV), 1.71 g (5.5 mmole) of (Z)-2-(benzoyloxymethyl) cyclohexylmethyl bromide (III), 1.38 g (10 mmole) of anhydrous potassium carbonate, 750 mg (5 mmole) of sodium iodide, and 7.5 ml of dry dimethyl sulfoxide was stirred under nitrogen and heated in an oil bath at 100° C. After 18 hours, during which the initially reddish-brown mixture gradually lightened in color and became thicker, the mixture was cooled, treated with 1 ml of glacial acetic acid, and stirred until gas evolution was complete.

The resulting mixture was then partitioned between 200 ml of ethyl acetate and 100 ml of water. The organic phase was washed with 6×100 ml of water, then dried over magnesium sulfate, and filtered with the filtrate being concentrated in vacuo (finally at ≦1 mm over a hot water bath) to give 1.30 g of light orange residual oil. The oil was dissolved in 4:1 hexane-acetone, which contained a minimum amount of methylene chloride and applied to a column of silica gel 60 (approx. 66×3.5 cm) packed in hexane. The column was eluted with 40:10:1 hexane-acetone-acetonitrile (2550 ml) followed by 30:10:1 hexane-acetone-acetonitrile.

Combined fractions 21–40 of 20–22 ml each, after the first 1500 ml was collected from the column, were concentrated in vacuo, and the residue was triturated with petroleum ether to give a solid, which was dried to yield 34 mg of off-white powder, mp 118.5–126.5°, homogeneous by TLC (30:10:1 hexane-acetone-acetonitrile), identified by spectra as 3-[(Z)-2-(benzoyloxymethyl)cyclohexylmethyl]thymine (VI). Combined fractions 65–100 were worked up as above to give 307 mg of white solid, mp 175°–178°, identified by spectra as 1-[(Z)-2-(benzoyloxymethyl)cyclohexylmethyl]thymine (V). This material was homogeneous by TLC (30:10:1 hexane-acetone-acetonitrile), with $R_f$ lower than that of VI. Mass spectra (FAB) of both V and VI were characterized by m/e 357 (MH+).

Selected 200 MHz $^1$H NMR data (in DMSO-d6; δ, ppm relative to Me4Si):

for V: 7.52 (s, 1H, partially obscured by aromatic resonances, pyrimidine $C^6$-H), 11.12 (s, 1H, $N^3$-H)

for VI: 7.25 (d, J=5.5 Hz, 1H, $C^6$-H; collapsed to singlet upon spiking with D2O), 10.79 (d, J=5.5 Hz, 1H, $N^1$-H) Selected UV data:

for V: $\lambda_{max}$ (MeOH) 272 nm (ε8540), $\lambda_{max}$ (MeOH+OH−) 271 nm (ε5910)

for VI: $\lambda_{max}$ (MeOH) 266 nm (ε6870), $\lambda_{max}$ (MeOH+OH−) 293nm (ε9220)

The UV spectra of V and VI are consistent with reported UV spectra for 1-methyl- and 3-methylthymine [T. Naito, M. Hirata, T. Kawakami, and M. Sano, Chem. Pharm. Bull., 9, 703 (1961); H. Tuppy and E Küchler, Monatsh Chem., 95, 1698 (1964)].

Elemental analysis: Calcd. for $C_{20}H_{24}N_2O_4$: C 67.39%; H, 6.79%; N, 7.86%. Found for V: C, 67.19%; H, 6.91%; N, 7.89%. Found for VI: C, 67.23%; H, 6.98%; N, 7.77%.

D. 1-[(Z)-2-(Hydroxymethyl)cyclohexylmethyl]thymine (VII)

A mixture of 178 mg (0.5 mmole) of 1-[(Z)-2-(benzoyloxymethyl)cyclohexylmethyl]thymine (V), 2 ml of 40% methylamine (aqueous), and 1 ml of methanol was stirred under gentle reflux in a nitrogen atmosphere until all of the solid dissolved. After 3 hours, when TLC (30:10:1 hexane-acetone-acetonitrile and 9:1 chloroform-methanol) indicated essentially complete reaction, the solution was cooled and concentrated in vacuo with the residual gum being crystallized from ether-acetone to give 80 mg (63%) of white crystals, mp 176°–178°, homogeneous by TLC (9:1 chloroform-methanol). Mass spectrum (FAB): m/e 253 (MH+). 200 MHz $^1$H NMR (DMSO-d6; selected peaks): δ1.74 (s, 3H, CH3), 3.3–3.6 (m, 2H, cyclohexyl-CH2N). 3.74 (dd, 2H, cyclohexyl-CH2O), 4.42 (t, 1H, OH), 7.47 (s, 1H, pyrimidine $C^6$-H), 10.10 (s, 1H, $N^3$-H), UV $\lambda_{max}$ (MeOH) 272 nm (ε9600), $\lambda_{max}$ (MeOH+H+) 272 nm (ε9680), $\lambda_{max}$ (MeOH+OH−) 270 nm (ε7110).

Elemental analysis: Calcd. for $C_{13}H_{20}N_2O_3$: C, 61.88%; H, 7.99%; N, 11.11%. Found: C, 61.90%; H, 8.03%; N, 11.06%.

What is claimed is:

1. A 1-[2-(hydroxymethyl)cycloalkylmethyl]-5-substituted-uracil of the formula:

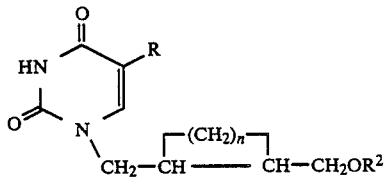

wherein R is H, halogen, $C_1$-$C_4$-straight or branched-chain alkyl, 2-halovinyl, or 2-haloethyl, n is 2 to 6; and $R^2$ is H or

where $R^1$ is $C_1$-$C_{12}$-straight or branched-chain alkyl or phenyl or naphthyl, or a pharmaceutically-acceptable salt thereof.

2. A 1-[2-(hydroxymethyl)cycloalkylmethyl]-5-substituted-uracil according to claim 1, which is
1-[(Z)-2-(hydroxymethyl)cyclobutylmethyl]thymine;
1-[(Z)-2-(hydroxymethyl)cyclopentylmethyl]thymine;
1-[(Z)-2-(hydroxymethyl)cyclohexylmethyl]thymine;
1-[(E)-2-(hydroxymethyl)cyclohexylmethyl]thymine;
1-[(Z)-2-(hydroxymethyl)cycloheptylmethyl]thymine;
1-[(Z)-2-(hydroxymethyl)cyclooctylmethyl]thymine;
5-bromo-1-[(Z)-2-(hydroxymethyl)cyclohexylmethyl]uracil;
5-ethyl-1-[(Z)-2-(hydroxymethyl)cyclohexylmethyl]uracil;
5-[(E)-2-bromovinyl]-1-[(Z)-2-(hydroxymethyl)cyclohexylmethyl]uracil; or
5-(2-chloroethyl)-1-[(Z)-2-(hydroxymethyl)cyclohexylmethyl]uracil.

3. A 1-[2-(hydroxymethyl)cycloalkylmethyl]5-substituted-uracil according to claim 2, which is
1-[(Z)-2-(hydroxymethyl)cyclohexylmethyl]thymine; or
5-[(E)-2-bromovinyl]-1-[(Z)-2-(hydroxymethyl)cyclohexylmethyl]-uracil.

4. A composition useful for imparting viral thymidine kinase-inhibiting activity comprising a carrier and a therapeutically-effective amount of a 1-[2-(hydroxymethyl)cycloalkylmethyl]-5-substituted-uracil according to claim 1.

5. A method fo treating herpes virus infections by inhibiting viral thymidine kinase activity in mammlian or avian species comprising administering a therapeutically-effective amount of a 1-[2-(hydroxymethyl)-cycloalkylmethyl]-5-substituted-uracil according to claim 1.

6. A method according to claim 5, wherein herpes virus infection thymidine kinase activity is inhibited, the therapeutically-effective amount is from 0.01 to about 200 mg/kg or body weight/day, the mammalian or avian species is a human being, and the uracil according to claim 1 is 1-[(Z)-2-(hydroxymethyl)cyclohexylmethyl] thymidine; or 5-[(E)-2-bromovinyl-1-[(Z)-2-hydroxymethyl)cyclohexylmethyl]uracil.

* * * * *

UNITED STATES PATENT AND TRADEMARK OFFICE
CERTIFICATE OF CORRECTION

PATENT NO. : 4,863,927

DATED : September 5, 1989

INVENTOR(S) : Richard L. Tolman and Wallace T. Ashton

It is certified that error appears in the above-identified patent and that said Letters Patent is hereby corrected as shown below:

IN THE TITLE

Please change "1-(2-HYDROXYMETHYL)CYCLOALKYLMETHYL)-5-SUBSTITUTED URACILS" to

"1-(2-(HYDROXYMETHYL)CYCLOALKYLMETHYL)-5-SUBSTITUTED URACILS".

Signed and Sealed this

Sixteenth Day of October, 1990

Attest:

HARRY F. MANBECK, JR.

Attesting Officer

Commissioner of Patents and Trademarks